US007795013B2

(12) United States Patent
Malmqvist et al.

(10) Patent No.: US 7,795,013 B2
(45) Date of Patent: Sep. 14, 2010

(54) HOLDER AND METHOD FOR COOLING OR HEATING SAMPLES

(75) Inventors: Mats Malmqvist, Uppsala (SE); Nicke Svanvik, Stockholm (SE); Fredrik Johnander, Linkoping (SE)

(73) Assignee: Alphahelix AB, Uppsala (SE)

( * ) Notice: Subject to any disclaimer, the term of this patent is extended or adjusted under 35 U.S.C. 154(b) by 1109 days.

(21) Appl. No.: 10/538,746

(22) PCT Filed: Dec. 15, 2003

(86) PCT No.: PCT/SE03/01953

§ 371 (c)(1),
(2), (4) Date: Apr. 3, 2006

(87) PCT Pub. No.: WO2004/056485

PCT Pub. Date: Jul. 8, 2004

(65) Prior Publication Data

US 2006/0199261 A1 Sep. 7, 2006

(30) Foreign Application Priority Data

Dec. 19, 2002 (SE) .................................... 0203781

(51) Int. Cl.
*C12M 1/00* (2006.01)
*C12M 3/00* (2006.01)

(52) U.S. Cl. ............... 435/303.1; 435/297.5; 435/305.1

(58) Field of Classification Search ..................... 435/6, 435/297.5, 303.1, 305.2
See application file for complete search history.

(56) References Cited

U.S. PATENT DOCUMENTS

| | | | | |
|---|---|---|---|---|
| 4,786,601 | A * | 11/1988 | Rothenberg | 435/305.2 |
| 5,504,007 | A | 4/1996 | Haynes | |
| 5,616,301 | A * | 4/1997 | Moser et al. | 422/104 |
| 5,942,432 | A * | 8/1999 | Smith et al. | 435/303.1 |
| 6,558,947 | B1 * | 5/2003 | Lund et al. | 435/303.1 |
| 2004/0149725 | A1 * | 8/2004 | Brown | 219/477 |

FOREIGN PATENT DOCUMENTS

| | | |
|---|---|---|
| EP | 1266691 | 12/2002 |
| WO | WO 137997 | 5/2002 |

* cited by examiner

*Primary Examiner*—Walter D Griffin
*Assistant Examiner*—Shanta G Doe
(74) *Attorney, Agent, or Firm*—Dowell & Dowell, P.C.

(57) ABSTRACT

A holder for a microtitreplate or an array of separate test tubes comprising a first panel (1) provided with a recess (2) for receiving each well (3) of the microtitreplate or test tubes and a second panel (7), which together with the first panel (1) and three side walls (5) form an inner space (8). The fourth side (9) comprises an inlet (10) for gas or liquid, whereby the gas or liquid entering the inner space (8) via the inlet (10) leaves the inner space (8) via said recesses (2), along the outside of the wells (3). A method for cooling or heating samples contained in wells (3) of a microtitreplate or an array of separate test tubes by inserting the microtitreplate or array of separate test tubes into such a holder and letting gas or liquid enter said inner space (8).

2 Claims, 3 Drawing Sheets

HOLDER AND METHOD FOR COOLING OR HEATING SAMPLES

CROSS REFERENCE TO RELATED APPLICATIONS

This application is a National Phase of PCT Application PCT/SE2003/001953 filed Dec. 15, 2003 in the name of Mats Malmqvist, Nicke Svanvik and Fredrik Johnander entitled, HOLDE AND METHOD FOR COOLING OR HEATING SAMPLES.

The present invention concerns a holder for a microtitreplate or for an array of separate test tubes and a method for cooling or heating samples contained in the wells of a microtitreplate or an array of separate test tubes.

BACKGROUND

In order to speed up chemical testing procedures there is an increasing demand for making manifold analyses in parallel. In typical cases such parallel analyses are performed in an array of separate test tubes or in different wells of a single unit called a microtitre plate.

A problem with such an approach arises during incubation, that is, when the samples are heated or cooled to desired reaction temperatures, which use to be referred to as "well-to-well uniformity". The problem is to expose the separate tubes or wells uniformly for the heating and cooling medium, often a gas or a liquid and to obtain homogeneous temperature within this medium.

The major source of poor thermal uniformity is the temperature gradients commonly established from the edges to the center of the tube array or the microtitre plate. Such gradients are more severe if the tubes or wells are obstacles for the flow of the medium, which often is the case.

SUMMARY OF THE INVENTION

The present invention aims to alleviate the above problems. The solution is provided by means of a holder for a microtitreplate or an array of separate test tubes having a first panel provided with a recess for receiving each well of the microtitreplate or test tubes and a second panel, which together with the first panel and three side walls forms an inner space, wherein a fourth side includes an inlet for gas or liquid, whereby the gas or liquid entering the inner space via the inlet leaves the inner space via the recesses along the outside of the wells. The solution is likewise provided by a method for cooling or heating samples contained in wells of a microtitreplate or an array of separate test tubes involving inserting the microtitreplate or array of separate test tubes into a holder described above.

An advantage with this is that the cooling or heating gas or liquid is spread evenly around each well providing a uniform heating or cooling of each sample in the microtitreplate or test tubes of the array.

The holder and method according to the present invention are especially advantageous when centrifuging microtitreplates or arrays of separate test tubes, for example, in a thermocycling device.

Tests have shown that systematic differences in temperature in the sample when using know technique to cool or heat samples in a microtitreplate or in an array of separate test tubes have been eliminated when using the present invention. Any small remaining differences are random instead of systematic.

SHORT DESCRIPTION OF THE DRAWINGS

The present invention will now be described by means of exemplifying embodiments in connection with the sketch drawings, in which.

DETAILED DESCRIPTION OF PREFERRED EMBODIMENTS

Figure 1:
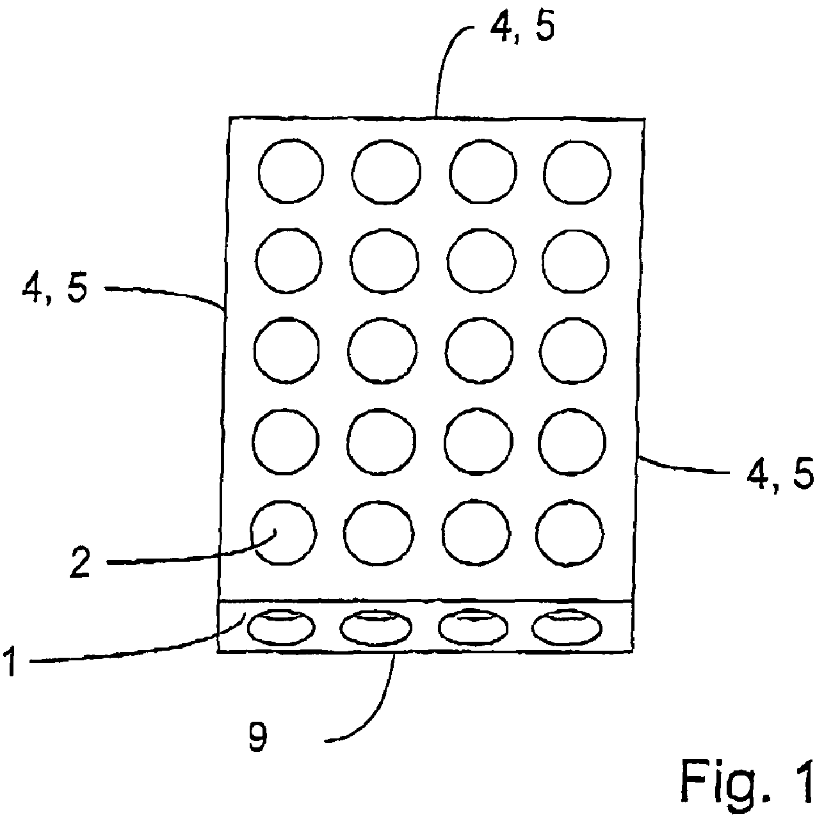
FIG. 1 illustrates in a plan view a holder according to an embodiment of the present invention.

A holder according to the present invention comprises a first panel 1, which preferably is substantially flat and for example made of a polymer material. The first panel 1 is provided with a number of recesses 2 adapted for receiving a well 3 of a microtitreplate 12 or a separate test tube. Preferably the number of recesses 2 corresponds to the number of wells 3 in a microtitreplate 12, for example 96.

Figure 3:
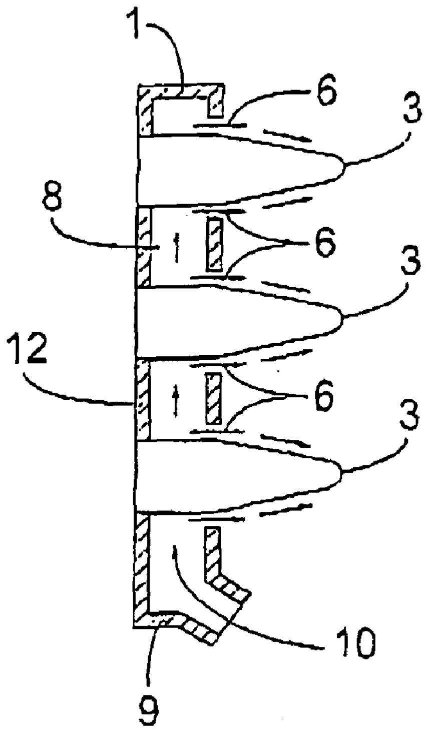
FIG. 3 illustrates in a cross sectional side view a holder according to an embodiment of the present invention with a microtitreplate arranged therein.
Figure 4:
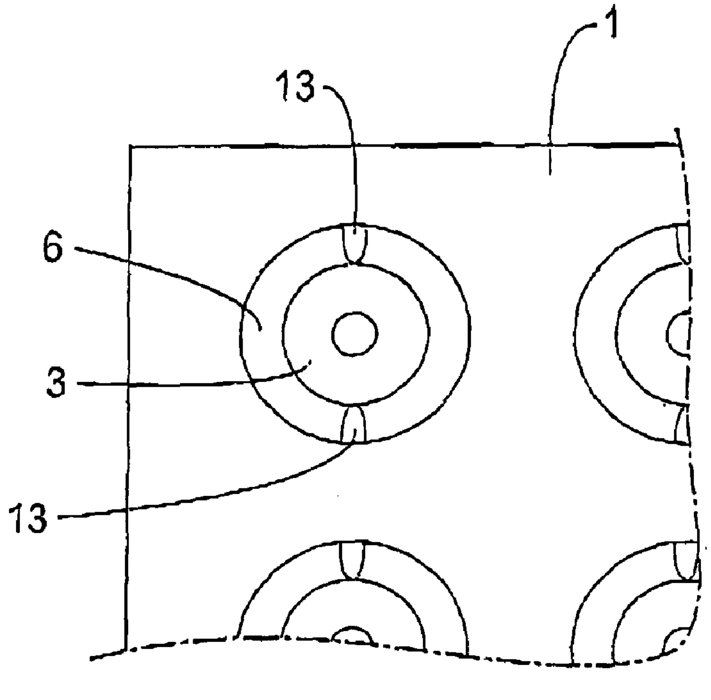
FIG. 4 illustrates in a plan view a detail of the holder with a microtitreplate arranged therein according to FIG. 1.
Figure 5:
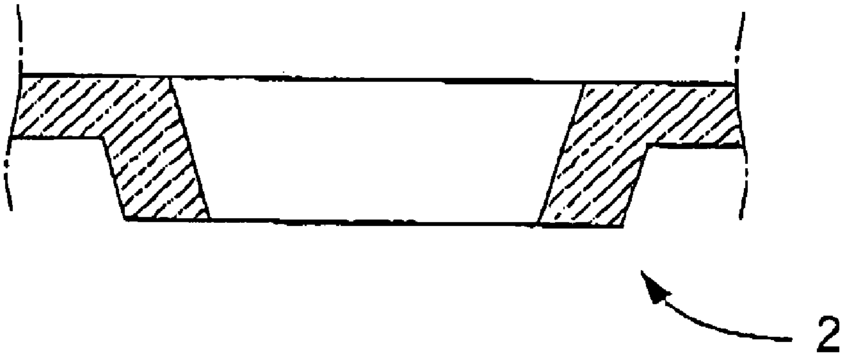
FIG. 5 illustrates in a cross sectional view an embodiment of a recess.
Figure 6:
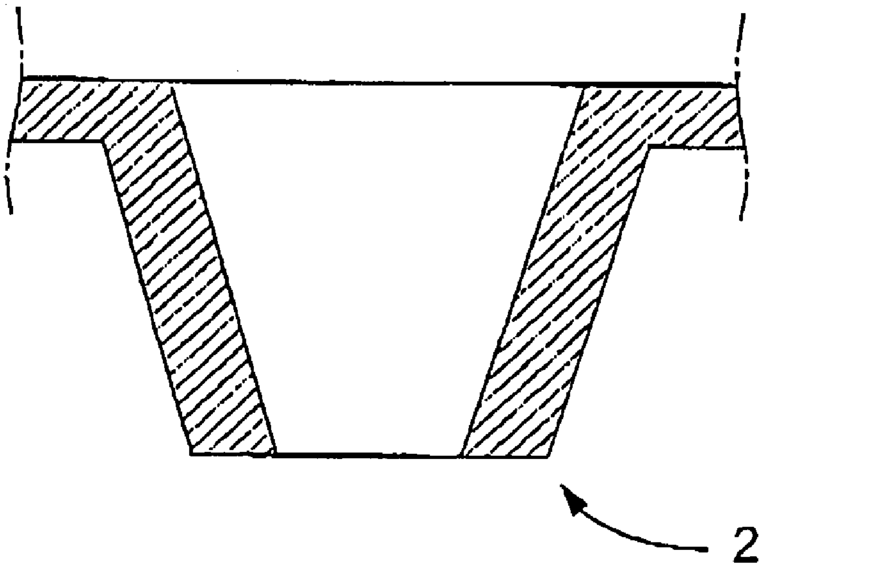
FIG. 6 illustrates in a cross sectional view another embodiment of a recess.

The recesses 2 may be through holes as illustrated in FIGS. 1-4 or dents or funnels as illustrated in FIGS. 5 and 6, respectively, having a hole in the bottom for gas or liquid to flow therethrough. Preferably the recesses 2 may have a shape of a circle, but may instead have shapes of an ellipse, square, rectangle or an octagon for example (not shown).

The first panel 1 has preferably a rectangular shape substantially corresponding to a microtitreplate 12. Along three of the edges 4 of the first panel 1 a side wall 5 is provided, which together with a second panel 7 forms an inner space 8 in the holder. The fourth edge 9 comprises an inlet opening 10 for cooling or heating gas or liquid.

Figure 2:
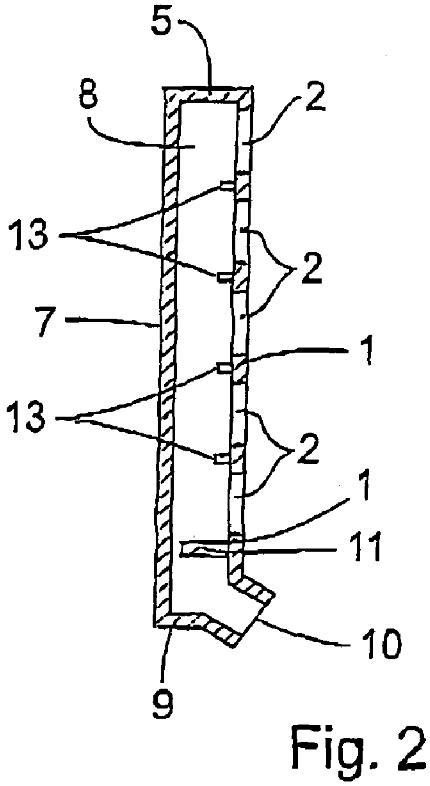
FIG. 2 illustrates in a cross sectional side view the holder according to FIG. 1.

The second panel 7 is preferably in the form of a lid, which is releasable attached, so that a microtitreplate 12 or separate test tubes may be inserted into the holder and the holder is closed by means of said lid 7 and thus forming the inner space 8, see FIG. 2. The lid 7 may be positioned so as to cover all the inlets of the wells 3 or be formed by a microtitreplate 12 itself as illustrated in FIG. 3.

The inlet opening 10 may extend along the whole side 9 of the first panel 10 or comprise several subopenings or extend along a part of the side 9 or be adapted in a suitable way for the specific use.

When cooling or heating the samples contained in the wells 3 cold or hot gas or liquid is made to flow into the inlet 10 of the holder so that the gas or liquid will flow around the upper portions of the wells 3 and fill the inner space 8. See arrows in FIG. 3.

The gas or liquid will then flow from the inner space 8 via gaps 6 between the recesses 2 and the wells 3 and further along the outside of the wells 3, thereby cooling or heating the samples inside the wells (3) in a homogeneous way.

In order to make sure that a gap 6 is provided between the recess 2 and the well 3, the edge may be provided with one or more protrusions 13, see FIGS. 2 and 4, protruding into the middle of the recess 2 or protruding from the inner side of the first panel 1, i.e. the side facing the microtitreplate 12 when it is arranged in the holder.

In case of the recesses 2 having a shape of a ellipse, for example, the protrusions may be missed out since the wells 3 would come into contact with the recesses 2 at two points of the elongated sides of the ellipse but there would still be a gap 6 around the rest of the circumference of the well 3.

Due to this or these protrusions 13 the microtitreplate 12 or the separate test tubes arranged in an array are prevented from reaching too close to the first side panel 1 so that the wells 3 would fill the whole recesses 2 and thus preventing the cooling or heating gas or liquid from flowing through the gap 6 along the outside of the wells 3.

In front of a first row of wells 3 of a microtitreplate 12 or an array of test tubes, seen in the flow direction, one or more baffles 11 may be arranged in order to spread the gas or liquid more evenly in the inner space 8 so that the first row will not be "hit" by all of the gas or liquid. See FIG. 2.

The invention claimed is:

1. A holder for microtitreplate (12) or an array of separate test tubes, comprising:

a first panel (1) provided with a recess (2) for receiving each well (3) of the microtitreplate (12) or test tubes and at least one protrusion (13) to secure a gap (6) between the wells (3) and the recesses (2); and a second panel (7), which together with the first panel (1) and three side walls (5) form an inner space (8), wherein the fourth side (9) includes an inlet (10) for gas or liquid, whereby the gas or liquid entering the inner space (8) via the inlet (10) leaves the inner space (8) via said recesses (2), along the outside of the wells (3).

2. A holder for microtitreplate (12) or an array of separate test tubes, comprising:

a first panel (1) provided with a recess (2) for receiving each well (3) of the microtitreplate (12) or test tubes;

a second panel (7), which together with the first panel (1) and three side walls (5) form an inner space (8), wherein the fourth side (9) includes an inlet (10) for gas or liquid, whereby the gas or liquid entering the inner space (8) via the inlet (10) leaves the inner space (8) via said recesses (2), along the outside of the wells (3); and at least one baffle (11) provided in front of the wells (3) positioned closest to the inlet (10) for gas or liquid.

* * * * *